(12) United States Patent
Little et al.

(10) Patent No.: US 10,493,025 B2
(45) Date of Patent: *Dec. 3, 2019

(54) NEUROMUSCULAR AID

(71) Applicant: CrampsAWAY Inc., Los Gatos, CA (US)

(72) Inventors: Jack E. Little, Los Gatos, CA (US); David Clarke, Los Gatos, CA (US); J. Gregory Little, Issaquah, WA (US)

(73) Assignee: CrampsAWAY Inc., Los Gatos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/049,418

(22) Filed: Jul. 30, 2018

(65) Prior Publication Data

US 2018/0333353 A1 Nov. 22, 2018

Related U.S. Application Data

(63) Continuation of application No. 15/066,864, filed on Mar. 10, 2016, now Pat. No. 10,034,831.

(60) Provisional application No. 62/131,202, filed on Mar. 10, 2015.

(51) Int. Cl.
| | |
|---|---|
| A61K 9/00 | (2006.01) |
| A61K 31/19 | (2006.01) |
| A61K 31/194 | (2006.01) |
| A61K 33/04 | (2006.01) |
| A61K 47/02 | (2006.01) |
| A61K 47/12 | (2006.01) |

(52) U.S. Cl.
CPC ............ *A61K 9/0053* (2013.01); *A61K 9/006* (2013.01); *A61K 31/19* (2013.01); *A61K 31/194* (2013.01); *A61K 33/04* (2013.01); *A61K 47/02* (2013.01); *A61K 47/12* (2013.01); *A61K 9/009* (2013.01)

(58) Field of Classification Search
CPC ...... A61K 31/19; A61K 31/194; A61K 33/04; A61K 47/02; A61K 47/12; A61K 9/0053; A61K 9/006; A61K 9/009
See application file for complete search history.

(56) References Cited

U.S. PATENT DOCUMENTS

| | | | | |
|---|---|---|---|---|
| 6,039,987 | A | 3/2000 | Strahl | |
| 6,348,506 | B2 | 2/2002 | Sneed | |
| 10,034,831 | B2* | 7/2018 | Little | A61K 9/0053 |
| 2004/0115247 | A1 | 6/2004 | Melman | |
| 2004/0176264 | A1 | 9/2004 | Song | |
| 2005/0282102 | A1* | 12/2005 | Kert | A61B 5/0088 |
| | | | | 433/29 |
| 2006/0172016 | A1 | 8/2006 | Kohutiak | |
| 2007/0270355 | A1 | 11/2007 | Garcia | |
| 2009/0162483 | A1 | 6/2009 | Constantine | |
| 2011/0313041 | A1 | 12/2011 | Minge | |
| 2012/0027693 | A1 | 2/2012 | Bean | |
| 2013/0059043 | A1 | 3/2013 | Hielscher | |
| 2016/0263025 | A1 | 9/2016 | Little | |

FOREIGN PATENT DOCUMENTS

| | | |
|---|---|---|
| WO | WO2007136284 A1 | 11/2007 |
| WO | WO2012015882 A1 | 2/2012 |
| WO | WO2016145225 A1 | 9/2016 |

OTHER PUBLICATIONS

Israelson-Harley (Desert News Utah, Aug. 2010, Pickle Juice doesn't cramp BYU football players' style) (Year: 2010).*
Authorized Officer Lee Ki Cheul, Korean Intellectual Property Office, International Search Report and Written Opinion for International Application No. PCT/US2016/021826, dated Sep. 7, 2016, 13 pages.
Forbes H. Norris et al. An Electromyographic Study of induced and spontaneous muscle cramps. Electroenceph Clin Neurophys 1957 9(suppl):139-47.
Markus Gulich et al. Epidemiology and determinants of nocturnal calf cramps. Eur J of Gen Prac 1998: 4(3): 109-13.
PHP Jansen et al. The Incidence of muscle cramps. J of Neurol, Neurosurg and Psych. 1991. 54(12): 1124-5.
A JJ Abdulla et al. Leg cramps in the elderly: prevalence, drug and disease associations. Internet J of Clin Prac. 1999;53(7): 494-6.
Timothy M. Miller et al. Muscle Cramps. Muscle Nerve. 2005;32: 431-42.
M.P. Schwellnus et al. Aetiology of skeletal muscles 'cramps' during exercise: A novel hypothesis. J Sports Sci Jun. 1997; 15(3): 277-85.
Marco Allessandro Minetto et al. Mechanisms of cramp contractions: peripheral or central general? J Physiol 2011 589;23: 5759-73.
MP Schwellnus. Cause of exercise associated muscles cramps (EAMC)—altered neuromuscular control, dehydration or electrolyte depletion? Br J Sport Med 2009;43(6): 401-8.
MP Schwellnus et al. Increased running speed and previous cramps rather than dehydration or serum sodium changes predict exercise-associated muscle cramping; a prospective cohort study in 210 human triathletes. Br J Sports Med Jun. 2011; 45(8): 650-6.

(Continued)

*Primary Examiner* — Mark V Stevens
(74) *Attorney, Agent, or Firm* — Fish & Richardson P.C.

(57) ABSTRACT

A neuromuscular aid for alleviation and prevention of conditions including muscle cramps and spasms. The neuromuscular aid may be in the form of a packet including a composition including 1 wt % to 15 wt % food grade acid. Instructions for use printed on an exterior of the packet include instructions to retain the composition in the oral cavity of a user for a length of time to alleviate or prevent muscle cramps. An oral treatment method includes administering a composition including 1 wt % to 15 wt % food grade acid to the oral cavity of a subject suffering from muscle cramps and retaining the composition in the oral cavity for a length of time. The composition may be in the form of a gas, a liquid, a solid, a gum, a powder, a thin film strip, a suspension, a colloid, or a gel.

25 Claims, 1 Drawing Sheet

(56) References Cited

OTHER PUBLICATIONS

MP Schwellnus et al. Serum electrolyte concentrations and hydration status are not associated with exercise associated muscles cramping (EAMC) in distance runners. Br J Sports Med 2004; 38:488-92.
Baldinger R et al. Treatment for cramps in amyotrophic lateral sclerosis/motor neuron disease. Cochrane Data Ser Apr. 2012 18:4.
Scott R. Garrison et al. Magnesium for skeletal muscle cramps. Cochrane Database Ser Sep. 2012.
Katzberg HD et al. Assessment: symptomatic treatment for muscle cramps (an evidence based review; report of the therapeutics and technology assessment subcommittee of the American Academy of Neurology. Neurol 2010; Feb. 23;74(8): 691-8.
RB Williams et al. Treatment of acute muscle cramps with pickle juice; a case report (abstract). Athlo Train 2000; 35 (supple):S24.
Kevin C. Miller et al. Athletic trainers' perception of pickle juice's effects on exercise associated muscle cramps. Athl Ther Today. 2008 13(5):31-4.
Kevin C. Miller et al. Electrolyte and plasma changes after pickle juice, water and a common carbohydrate electrolyte solution. J Athl Train 2009; 44(5): 454-61.
Kevin C. Miller et al. Gastric Empyting after Pickle-Juice Ingestion in Rested, Euhydrated Humans. J Athl Train 2010; 45(6): 601-8.
Kevin C. Miller et al. Exercise-Associated muscle cramping: Causes, Treatment and Prevention. Sport Health 2010; 2(4): 279-83.
Reynolds (New York Times blog, Well, Jun. 2010, https://well.blogs.nytimes.com/2010/06/09/phys-ed-can-pickle-juice-stopmuscle-cramps/).

* cited by examiner

NEUROMUSCULAR AID

CROSS-REFERENCE TO RELATED APPLICATION

This application is a continuation of U.S. application Ser. No. 15/066,864 filed on Mar. 10, 2016, which claims priority to U.S. Application Ser. No. 62/131,202 filed on Mar. 10, 2015, which are incorporated herein by reference in their entirety.

TECHNICAL FIELD

The present invention relates to neuromuscular aid for alleviation and prevention of conditions including muscle cramps and muscle spasms.

BACKGROUND

Muscle cramps, or the involuntary contraction of muscles lasting seconds or minutes, are common. Exercise-associated muscle cramps (EAMC) are painful, and usually necessitate the subject (e.g., athlete) to cease the motions that initiated the cramps. For professional athletes, muscles cramps can have devastating and costly consequences, but most people who have cramps describe the experience as painful and would prefer the cramp be alleviated quickly or prevented altogether. Muscle cramps that occur during sleep lead to poor sleep (quality) and sleep deprivation (quantity) and therefore contribute to excessive daytime somnolence. Muscles cramps also commonly occur in association with systemic diseases or conditions or treatments for these diseases. A partial list of these includes lower motor neuron disease, upper motor neuron disease, post-poliomyelitis, uremia, cirrhosis, hypothyroidism, pregnancy, diarrhea, and hemodialysis. Because muscle cramps are ubiquitous, cause pain and suffering, cause sleep disturbance, and impair athletic performance, rapid and reliable treatment and prevention are needed.

SUMMARY

Compositions and methods of the present disclosure benefit from a recognition that a neuromuscular condition may be alleviated or prevented by contacting receptors (e.g., chemoreceptors and neuroreceptors) in the oral cavity of a user with a neuromuscular aid. In so doing, efficient delivery of the neuromuscular aid is achieved to rapidly and reliably alleviate or prevent the neuromuscular condition. In one example, a neuromuscular aid including a food grade acid can be used to rapidly and reliably alleviate muscle cramps.

In a first general aspect, a neuromuscular aid includes 1 wt % to 15 wt % food grade acid.

Implementations of the first general aspect may include one or more of the following features.

The food grade acid may include at least one of acetic acid, citric acid, sulfuric acid, and lactic acid. In one example, the food grade acid is acetic acid. In another example, the food grade acid is a mixture of acetic acid and citric acid. In yet another example, the food grade acid is a mixture of any three of acetic acid, citric acid, sulfuric acid, and lactic acid. In yet another example, the food grade acid is a mixture of acetic acid, citric acid, sulfuric acid, and lactic acid.

The neuromuscular aid may include 1 wt % to 10 wt %, 2 wt % to 8 wt %, 3 wt % to 6 wt %, or 4 wt % to 5 wt % of the food grade acid.

The neuromuscular aid may include electrolytes. The electrolytes may include at least one of potassium, calcium, and sodium. In one example, the neuromuscular aid includes potassium. In another example, the neuromuscular aid includes calcium. In yet another example, the neuromuscular aid includes potassium, calcium, and sodium. In yet another example, the neuromuscular aid may be free of sodium (e.g., free of added sodium). In some cases, electrolytes are present in a total amount of up to 1 wt %. In certain cases, each of one or more electrolytes is present in an amount of 0.01 wt % to 0.5 wt %.

The neuromuscular aid may include a flavoring. The flavoring may be natural or artificial. The flavoring may be at least one of a lemon, orange, cinnamon, ginger, berry, and mint flavoring. In one example, the flavoring includes a lemon flavoring and an orange flavoring.

The neuromuscular aid may include a thickening agent, an emulsifier, or both.

A single dose of the neuromuscular aid may include 1 mL to 50 mL, 3 mL to 30 mL, or 5 mL to 10 mL of the neuromuscular aid.

The neuromuscular aid may alleviate or prevent muscle cramps.

The neuromuscular aid may include instructions for use. Instructions for use of the neuromuscular aid may include instructions to retain the neuromuscular aid in the oral cavity for 5 seconds to 120 seconds, 10 seconds to 60 seconds, or up to 60 seconds. The instructions for use may include instructions to expel the neuromuscular aid from the oral cavity. In one example, the instructions for use include instructions to retain the neuromuscular aid in the oral cavity for 5 seconds to 120 seconds and expel the neuromuscular aid from the oral cavity after retaining the neuromuscular aid in the oral cavity for 5 seconds to 120 seconds. In another example, the instructions for use include instructions to retain the neuromuscular aid in the oral cavity for 10 seconds to 60 seconds and expel the neuromuscular aid from the oral cavity after retaining the neuromuscular aid in the oral cavity for 10 seconds to 60 seconds.

The instructions for use may include instructions to swallow or ingest the neuromuscular aid. In one example, the instructions for use include instructions to retain the neuromuscular aid in the oral cavity for 5 seconds to 120 seconds and ingest or swallow the neuromuscular aid after retaining the neuromuscular aid in the oral cavity for 5 seconds to 120 seconds. In another example, the instructions for use include instructions to retain the neuromuscular aid in the oral cavity for 10 seconds to 60 seconds and ingest or swallow the neuromuscular aid after retaining the neuromuscular aid in the oral cavity for 10 seconds to 60 seconds.

The instructions for use may include instructions to gargle with the oral rinse or swish the neuromuscular aid in the oral cavity. In one example, the instructions for use include instructions to gargle with the oral rinse or swish neuromuscular aid in the oral cavity for 5 seconds to 120 seconds and expel the neuromuscular aid from the oral cavity. In another example, the instructions for use include instructions to gargle with the neuromuscular aid or swish the neuromuscular aid in the oral cavity for 10 seconds to 60 seconds and expel the neuromuscular aid from the oral cavity. In yet another example, the instructions for use include instructions to gargle with the neuromuscular aid or swish the neuromuscular aid in the oral cavity for 5 seconds to 120 seconds and ingest or swallow the neuromuscular aid. In another example, the instructions for use include instructions to gargle with the neuromuscular aid or swish the neuromuscular aid in the oral cavity for 10 seconds to 60 seconds and swallow or ingest the neuromuscular aid.

The instructions for use may include instructions to retain the neuromuscular aid in the oral cavity until muscle cramps subside. In one example, the instructions for use include instructions to retain the neuromuscular aid in the oral cavity until muscle cramps subside and then expel the neuromuscular aid from the oral cavity. In another example, the instructions for use include instructions to retain the neuromuscular aid in the oral cavity until muscle cramps subside and then swallow or ingest the neuromuscular aid.

In a second general aspect, an oral rinse for alleviating or preventing muscle cramps includes 1 wt % to 15 wt % food grade acid.

Implementations of the second general aspect may include one or more of the following features.

The food grade acid may include at least one of acetic acid, citric acid, sulfuric acid, and lactic acid. In one example, the food grade acid is acetic acid. In another example, the food grade acid is a mixture of acetic acid and citric acid. In yet another example, the food grade acid is a mixture of any three of acetic acid, citric acid, sulfuric acid, and lactic acid. In yet another example, the food grade acid is a mixture of acetic acid, citric acid, sulfuric acid, and lactic acid.

The oral rinse may include 1 wt % to 10 wt %, 2 wt % to 8 wt %, 3 wt % to 6 wt %, or 4 wt % to 5 wt % of the food grade acid.

The oral rinse may include electrolytes. The electrolytes may include at least one of potassium, calcium, and sodium. In one example, the oral rinse includes potassium. In another example, the oral rinse includes calcium. In yet another example, the oral rinse include potassium, calcium, and sodium. In yet another example, the oral rinse may be free of sodium (e.g., free of added sodium). In some cases, electrolytes are present in a total amount of up to 1 wt %. In certain cases, each of one or more electrolytes is present in an amount of 0.01 wt % to 0.5 wt %.

The oral rinse may include a flavoring. The flavoring may be natural or artificial. The flavoring may be at least one of a lemon, orange, cinnamon, ginger, berry, and mint flavoring. In one example, the flavoring includes a lemon flavoring and an orange flavoring.

The oral rinse may include a thickening agent, an emulsifier, or both.

The single dose of the oral rinse may include 1 mL to 50 mL, 3 mL to 30 mL, or 5 mL to 10 mL of the oral rinse.

The oral rinse may include instructions for use. The instructions for use may include instructions to retain the oral rinse in the oral cavity for 5 seconds to 120 seconds, 10 seconds to 60 seconds, or up to 60 seconds. The instructions for use may include instructions to expel the oral rinse from the oral cavity. In one example, the instructions for use include instructions to retain the oral rinse in the oral cavity for 5 seconds to 120 seconds and expel the oral rinse from the oral cavity after retaining the oral rinse in the oral cavity for 5 seconds to 120 seconds. In another example, the instructions for use include instructions to retain the oral rinse in the oral cavity for 10 seconds to 60 seconds and expel the oral rinse from the oral cavity after retaining the oral rinse in the oral cavity for 10 seconds to 60 seconds.

The instructions for use may include instructions to swallow or ingest the oral rinse. In one example, the instructions for use include instructions to retain the oral rinse in the oral cavity for 5 seconds to 120 seconds and ingest or swallow the oral rinse after retaining the oral rinse in the oral cavity for 5 seconds to 120 seconds. In another example, the instructions for use include instructions to retain the oral rinse in the oral cavity for 10 seconds to 60 seconds and ingest or swallow the oral rinse after retaining the oral rinse in the oral cavity for 10 seconds to 60 seconds.

The instructions for use may include instructions to gargle with the oral rinse or swish the oral rinse in the oral cavity. In one example, the instructions for use include instructions to gargle with the oral rinse or swish the oral rinse in the oral cavity for 5 seconds to 120 seconds and expel the oral rinse from the oral cavity. In another example, the instructions for use include instructions to gargle with the oral rinse or swish the oral rinse in the oral cavity for 10 seconds to 60 seconds and expel the oral rinse from the oral cavity. In yet another example, the instructions for use include instructions to gargle with the oral rinse or swish the oral rinse in the oral cavity for 5 seconds to 120 seconds and ingest or swallow the oral rinse. In another example, the instructions for use include instructions to gargle with the oral rinse or swish the oral rinse in the oral cavity for 10 seconds to 60 seconds and swallow or ingest the oral rinse.

The instructions for use may include instructions to retain the neuromuscular aid in the oral cavity until muscle cramps subside. In one example, the instructions for use include instructions to retain the oral rinse in the oral cavity until muscle cramps subside and then expel the oral rinse from the oral cavity. In another example, the instructions for use include instructions to retain the oral rinse in the oral cavity until muscle cramps subside and then swallow or ingest the oral rinse.

In a third general aspect, a packet includes a composition including 1 wt % to 15 wt % food grade acid. Instructions for use are printed on an exterior of the packet. The instructions for use include instructions to retain the composition in the oral cavity of a subject for a length of time to alleviate or prevent muscle cramps.

Implementations of the third general aspect may include one or more of the following features.

The food grade acid may include at least one of acetic acid, citric acid, sulfuric acid, and lactic acid. In one example, the food grade acid is acetic acid. In another example, the food grade acid is a mixture of acetic acid and citric acid. In yet another example, the food grade acid is a mixture of three of acetic acid, citric acid, sulfuric acid, and lactic acid. In yet another example, the food grade acid is a mixture of acetic acid, citric acid, sulfuric acid, and lactic acid.

The composition may be in the form of a gas, a liquid, a solid, a gum, a powder, a thin film strip, a suspension, a colloid, or a gel. The liquid may be a carbonated liquid.

The composition may include 1 wt % to 10 wt %, 2 wt % to 8 wt %, 3 wt % to 6 wt %, or 4 wt % to 5 wt % of the food grade acid.

The packet may include a single dose of the composition.

The instructions for use may include instructions to expel the composition from the oral cavity. The instructions for use may include instructions to retain the composition in the oral cavity for 5 seconds to 120 seconds or 10 seconds to 60 seconds The composition may be in the form of an oral rinse. The oral rinse may be an aqueous solution.

The oral rinse may include electrolytes. The electrolytes may include at least one of potassium, calcium, and sodium. In one example, the oral rinse includes potassium. In another example, the oral rinse includes calcium. In yet another example, the oral rinse include potassium, calcium, and sodium. In yet another example, the oral rinse may be free of sodium. In some cases, electrolytes are present in a total amount of up to 1 wt %. In certain cases, each of one or more electrolytes is present in an amount of 0.01 wt % to 0.5 wt %.

The oral rinse may include a flavoring. The flavoring may be natural or artificial. The flavoring may be at least one of a lemon, orange, cinnamon, ginger, berry, and mint flavoring. In one example, the flavoring includes a lemon flavoring and an orange flavoring.

The oral rinse may include a thickening agent, an emulsifier, or both.

The single dose of the oral rinse may include 1 mL to 50 mL, 3 mL to 30 mL, or 5 mL to 10 mL of the oral rinse.

The instructions for use may include instructions to rinse the oral cavity with the oral rinse. In one example, the instructions for use include instructions to expel the oral rinse from the oral cavity after rinsing the oral cavity with the oral rinse for 5 seconds to 120 seconds or 10 seconds to 60 seconds.

The instructions for use may include instructions to retain the oral rinse in the oral cavity for 5 seconds to 120 seconds, 10 seconds to 60 seconds, or up to 60 seconds.

The instructions for use may include instructions to expel the oral rinse from the oral cavity. In one example, the instructions for use include instructions to retain the oral rinse in the oral cavity for 5 seconds to 120 seconds and expel the oral rinse from the oral cavity after retaining the oral rinse in the oral cavity for 5 seconds to 120 seconds. In another example, the instructions for use include instructions to retain the oral rinse in the oral cavity for 10 seconds to 60 seconds and expel the oral rinse from the oral cavity after retaining the oral rinse in the oral cavity for 10 seconds to 60 seconds.

The instructions for use may include instructions to swallow or ingest the oral rinse. In one example, the instructions for use include instructions to retain the oral rinse in the oral cavity for 5 seconds to 120 seconds and ingest or swallow the oral rinse after retaining the oral rinse in the oral cavity for 5 seconds to 120 seconds. In another example, the instructions for use include instructions to retain the oral rinse in the oral cavity for 10 seconds to 60 seconds and ingest or swallow the oral rinse after retaining the oral rinse in the oral cavity for 10 seconds to 60 seconds.

The instructions for use may include instructions to gargle with the oral rinse or swish the oral rinse in the oral cavity. In one example, the instructions for use include instructions to gargle with the oral rinse or swish the oral rinse in the oral cavity for 5 seconds to 120 seconds and expel the oral rinse from the oral cavity. In another example, the instructions for use include instructions to gargle with the oral rinse or swish the oral rinse in the oral cavity for 10 seconds to 60 seconds and expel the oral rinse from the oral cavity. In yet another example, the instructions for use include instructions to gargle with the oral rinse or swish the oral rinse in the oral cavity for 5 seconds to 120 seconds and ingest or swallow the oral rinse. In another example, the instructions for use include instructions to gargle with the oral rinse or swish the oral rinse in the oral cavity for 10 seconds to 60 seconds and swallow or ingest the oral rinse.

The instructions for use may include instructions to retain the neuromuscular aid in the oral cavity until muscle cramps subside. In one example, the instructions for use include instructions to retain the oral rinse in the oral cavity until muscle cramps subside and then expel the oral rinse from the oral cavity. In another example, the instructions for use include instructions to retain the oral rinse in the oral cavity until muscle cramps subside and then swallow or ingest the oral rinse.

In a fourth general aspect, an oral treatment method includes administering a composition comprising 1 wt % to 15 wt % food grade acid to the oral cavity of a subject suffering from muscle cramps, and retaining the composition in the oral cavity for 5 seconds to 120 seconds.

Implementations of the fourth general aspect may include one or more of the following features.

The composition may be an oral rinse. The composition may be in the form of a gas, a liquid, a carbonated liquid, a solid, a gum, a powder, a thin film strip, a suspension, a colloid, or a gel.

The oral treatment method may include retaining the composition in the oral cavity for 10 seconds for 60 seconds.

The oral treatment method may include expelling the oral rinse from the oral cavity after retaining the oral rinse in the oral cavity for 5 seconds to 120 seconds or expelling the oral rinse from the oral cavity after retaining the oral rinse in the oral cavity for 10 seconds to 60 seconds.

The oral treatment method may include ingesting or swallowing the oral rinse after retaining the oral rinse in the oral cavity for 5 seconds to 120 seconds or ingesting or swallowing the oral rinse after retaining the oral rinse in the oral cavity for 10 seconds to 60 seconds.

A fifth general aspect includes the use of a neuromuscular aid to alleviate or prevent neuromuscular conditions.

Implementations of the fifth general aspect may include one or more of the following features.

The neuromuscular aid may include a food grade acid. The food grade acid may include at least one of acetic acid, citric acid, sulfuric acid, and lactic acid. In one example, the food grade acid is acetic acid. In another example, the food grade acid is a mixture of acetic acid and citric acid. In yet another example, the food grade acid is a mixture of three of acetic acid, citric acid, sulfuric acid, and lactic acid. In yet another example, the food grade acid is a mixture of acetic acid, citric acid, sulfuric acid, and lactic acid. The neuromuscular aid may include 1 wt % to 15 wt %, 1 wt % to 10 wt %, 2 wt % to 8 wt %, 3 wt % to 6 wt %, or 4 wt % to 5 wt % of a food grade acid.

The neuromuscular aid may include electrolytes. The electrolytes may include at least one of potassium, calcium, and sodium. In one example, the neuromuscular aid includes potassium. In another example, the neuromuscular aid includes calcium. In yet another example, the neuromuscular aid includes potassium, calcium, and sodium. In yet another example, the neuromuscular aid may be free of sodium (e.g., free of added sodium). In some cases, electrolytes are present in a total amount of up to 1 wt %. In certain cases, one or more electrolytes are each present in an amount of 0.01 wt % to 0.5 wt %.

The neuromuscular aid may include a flavoring. The flavoring may be natural or artificial. The flavoring may be at least one of a lemon, orange, cinnamon, ginger, berry, and mint flavoring. In one example, the flavoring includes a lemon flavoring and an orange flavoring.

The neuromuscular aid may include a thickening agent, an emulsifier, or both.

A single dose of the neuromuscular aid may include 1 mL to 50 mL, 3 mL to 30 mL, or 5 mL to 10 mL of the neuromuscular aid.

The neuromuscular aid may alleviate or prevent muscle cramps.

The neuromuscular aid may be an oral rinse. The neuromuscular aid may be in the form of a solid, a gum, a powder, a thin film strip, a suspension, a colloid, or a gel.

Use of the neuromuscular aid may include retaining the neuromuscular aid in the oral cavity for 5 seconds to 120 seconds or 10 seconds to 60 seconds.

Use of the neuromuscular aid may include expelling the neuromuscular aid from the oral cavity after retaining the neuromuscular aid in the oral cavity for 5 seconds to 120 seconds or expelling the neuromuscular aid from the oral cavity after retaining the neuromuscular aid in the oral cavity for 10 seconds to 60 seconds.

Use of the neuromuscular aid may include ingesting or swallowing the neuromuscular aid after retaining the neuromuscular aid in the oral cavity for 5 seconds to 120 seconds or ingesting or swallowing the neuromuscular aid after retaining the neuromuscular aid in the oral cavity for 10 seconds to 60 seconds.

Thus, particular embodiments have been described. Variations, modifications, and enhancements of the described embodiments and other embodiments can be made based on what is described and illustrated. In addition, one or more features of one or more embodiments may be combined. The details of one or more implementations and various features and aspects are set forth in the accompanying drawings, the description, and the claims below.

DETAILED DESCRIPTION

Figure 1:
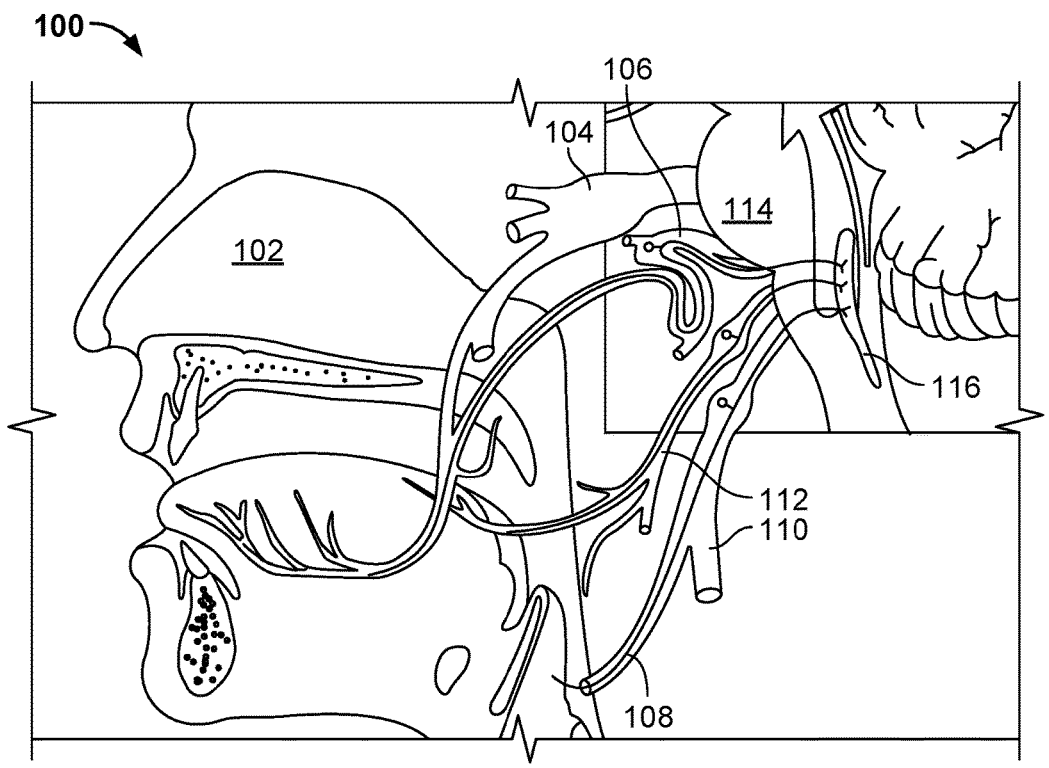
FIG. 1 depicts a lateral view of an oral cavity and associated nerves.

Two simultaneous events are believed to contribute to muscle cramping. First, neuromuscular fatigue leads to a susceptibility for a muscle group to cramp. The cramping is caused by massive neurostimulation of the muscle, originating in the spinal cord, which prolongs painful muscle contraction. Second, the simultaneous inhibition of the opposing muscle group allows the cramp to be sustained. Under normal circumstances, a massive muscle contraction should cause Golgi receptors in the opposing muscle group to fire; however, in the case of muscle cramps, the neuromuscular unit in the opposing muscle is inhibited. Thus, muscle cramps can be understood as occurring at the junction of a nerve and a muscle.

As described herein, a neuromuscular aid is used to stimulate the neuromuscular unit being inhibited in the cramping process to reliably and quickly alleviate the cramp. The neuromuscular aid provides a food grade acid in a concentration between 0.1 wt % and 15 wt % (e.g., 1 wt % to 15 wt %, 1 wt % to 10 wt %, 2 wt % to 8 wt %, 3 wt % to 6 wt %, or 4 wt % to 5 wt %) to the oral cavity of a user. Suitable food grade acids include acetic acid, citric acid, sulfuric acid, lactic acid, and the like. In some embodiments, a neuromuscular aid includes one or more additives such as vitamins, electrolytes, sweetener, coloring agents, preservatives, thickening agents, flavorings, and the like. Suitable vitamins include water-soluble vitamins such as B vitamins (e.g., riboflavin ($B_1$), thiamin ($B_2$), niacin ($B_3$), vitamin $B_6$, vitamin $B_{12}$, folic acid, pantothenic acid, and biotin) and vitamin C. Suitable electrolytes include potassium, calcium, and sodium. In some cases, electrolytes are present in a total amount of up to 1 wt %. In certain cases, each of one or more electrolytes is present in an amount of 0.01 wt % to 0.5 wt %. Suitable thickening agents include polysaccharides (e.g., starches, vegetable gums, and pectin) and proteins (e.g., collagen, egg whites, and gelatin). Suitable flavorings include natural and artificial lemon, orange, cinnamon, ginger, berry, and mint flavoring. A pH of the neuromuscular aid may be in a range of 2 to 6 or 3 to 5 or may be selected to create a pH of 2 to 6 or 3 to 5 in the oral cavity of a subject. The neuromuscular aid may be free of sodium (e.g., free of added sodium).

A neuromuscular aid may be in the form of a gas, liquid, carbonated liquid, solid, gum, candy, thin film, gel, spray, suspension, colloid, or aerosol, such that a concentration of the food grade acid in the oral cavity is 1 wt % to 15 wt % upon administration or over time. In one example, a solid candy includes sugar, corn syrup, water, and a food grade acid that is released over time to yield food grade acid in a concentration of 1 wt % to 15 wt % when combined with saliva in the oral cavity of a subject. In another example, a gum includes gum base, sweetener, flavoring, coloring, and food grade acid that is released over time to yield food grade acid in a concentration of 1 wt % to 15 wt % when combined with saliva in the oral cavity of a subject.

In one embodiment, the neuromuscular aid is an aerosol that is pumped or sprayed into the oral cavity of a subject. The neuromuscular aid may be held, swished, or gargled for a length of time (e.g., 60 seconds) and then expelled from the oral cavity. In one example, an aerosol neuromuscular aid includes 10 wt % acetic acid and, when mixed with saliva in the oral cavity of a subject, yields a solution of about 6 wt % acetic acid. In another example, an aerosol neuromuscular aid is an aqueous solution including 15 wt % citric acid and orange flavoring.

In one embodiment, the neuromuscular aid is an oral rinse. The oral rinse is typically an aqueous composition including 1 wt % and 15 wt % (e.g., 1 wt % to 10 wt %, 2 wt % to 8 wt %, 3 wt % to 6 wt %, or 4 wt % to 5 wt %) of food grade acid. The oral rinse may be an aqueous solution. In one example, an oral rinse includes 3 wt % to 6 wt % of acetic acid. In another example, an oral rinse includes 3 wt % to 6 wt % of acetic acid and citric acid. An oral rinse may include one or more additives such as vitamins, minerals, sweetener, coloring agents, preservatives, thickening agents, flavorings, and the like as described herein. A pH of the neuromuscular aid may be in a range of 2 to 6 or 3 to 5 or may be selected to create a pH of 2 to 6 or 3 to 5 in the oral cavity of a subject.

A neuromuscular aid may be administered to the oral cavity of a subject suffering from muscle cramps. In some cases, the neuromuscular aid is administered to the oral cavity of a subject for the prevention of muscle cramps. The neuromuscular aid is held in the oral cavity of the subject for a length of time such that all or most of the oral cavity and tongue are in contact with the oral rinse. Holding the neuromuscular aid in the oral cavity may include at least one of swishing the neuromuscular aid in the oral cavity and gargling with the neuromuscular aid. In some cases, the neuromuscular aid is expelled from the oral cavity after the neuromuscular aid is held in the oral cavity for the length of time. If desired, the neuromuscular aid may be ingested after being held in the oral cavity for the length of time.

Continuous and repeated stimulation of the nerves by a neuromuscular aid held in the oral cavity for a length of time, rather than incidental contact when being swallowed, creates a biological change or response to targeted anatomy more quickly, fully, and efficiently and less invasively than swallowing the neuromuscular aid. While being held in the oral cavity, the nerves that control a range of involuntary responses are stimulated, causing relief of maladies such as cramping.

Swishing, holding, or gargling a neuromuscular aid in the mouth, as opposed to swallowing, allows subjects with a delicate gag reflex, sensitive digestive tract, or sore throat to avoid ingestion of the neuromuscular aid while still benefiting from it. This is especially important for subjects whose digestive systems have been compromised by therapies such as chemotherapy.

Certain chemicals take longer than others to stimulate chemoreceptors. Substances such as acids, drugs, vitamins, or other medicinal solutions that are held, swished, or gargled in the oral cavity, rather than ingested, create a biological response that may be manifested more quickly. These biological changes may be effected in systems of the subject including, but not limited to, the nervous system, the endocrine system, the digestive system, the urinary system, the respiratory system, the circulatory system, the lymphatic system, the immune system, the reproductive system, the muscular system, the skeletal system, and the integumentary system. These systems may all be affected simultaneously or individually depending on the application, subject, and formulation.

A neuromuscular aid is typically held in the oral cavity for 5 seconds to 120 seconds (e.g., 10 seconds to 60 seconds, up to 20 seconds, up to 40 seconds, or up to 60 seconds), or for a length of time required to alleviate cramping symptoms. The frequency of use and length of time held in the oral cavity may be adjusted depending on the subject, location of cramp, application, and formulation of the neuromuscular aid. In one example, a shorter length of time may be required for a child to experience relief of symptoms than an adult male. In another example, a longer length of time may be required for a cramp in a foot than a cramp in the neck. Typically, a neuromuscular aid having a higher concentration requires a shorter length of time than a neuromuscular aid having a lower concentration.

Holding the neuromuscular aid in the oral cavity stimulates receptors on the tongue, posterior pharynx, and other surfaces in the mouth, as well as receptors throughout the gastrointestinal tract. FIG. 1 depicts a lateral view of a human oral cavity 100 and associated nerves, including the chorda tympani nerve 102, trigeminal ganglion 104, facial nerve 106, superior laryngeal nerve 108, vagus nerve 110, and glossopharyngeal nerve 112. The brain stem 114 and solitary tract nucleus 116 are also depicted. The stimulation of these receptors leads to a neuronal discharge from the spinal cord to the opposing muscle group, thus allowing the cramping muscle to stretch and cease cramping. In some cases, a neuromuscular aid may inhibit spinal cord neuronal impulses that initiate and maintain muscle cramping.

As described herein, a neuromuscular aid relieves, alleviates, ameliorates, and/or prevents muscle cramps, including cramps that occur, for example, during exertion, resting, night time, and menstruation, and may promote relief of generalized pain from muscle spasms and muscle fatigue, headaches associated with muscle tension and generalized pain associated with premenstrual syndrome, fibromyalgia, and treatments and systemic diseases or that cause muscular aches or pains. The neuromuscular aid stimulates the neuromuscular unit being inhibited in the cramping process, thereby reliably and quickly alleviating the cramp.

Testing has shown that swishing a neuromuscular aid that stimulates the nerves, chemoreceptors, and/or taste buds in the mouth typically brings about faster biological responses or changes to certain anatomy than swallowing the same substance. For example, the effectiveness of swishing a neuromuscular aid in the mouth and expelling the solution after 60 seconds has been shown on multiple occasions with multiple test subjects. In the case of cramp relief, subjects have consistently gotten relief from muscle cramps in less than one minute of swishing a neuromuscular aid specifically formulated for swishing, whereas swallowing the same neuromuscular aid brought similar relief after more than 2 to 5 minutes.

A neuromuscular aid may be packaged to provide multiple doses or a single dose. In one embodiment, a neuromuscular aid in the form of a gas, liquid, carbonated liquid, spray, or aerosol is provided in a single package (e.g., a bottle) that yields at least 10, 20, or 30 doses. In another embodiment, a neuromuscular aid in the form of a liquid, solid, gum, candy, thin film, or gel is packaged as a single dose. Packaging for the neuromuscular aid typically includes instructions for use. In one example, instructions for use of a neuromuscular aid are printed on the exterior of the packaging.

Figure 2:
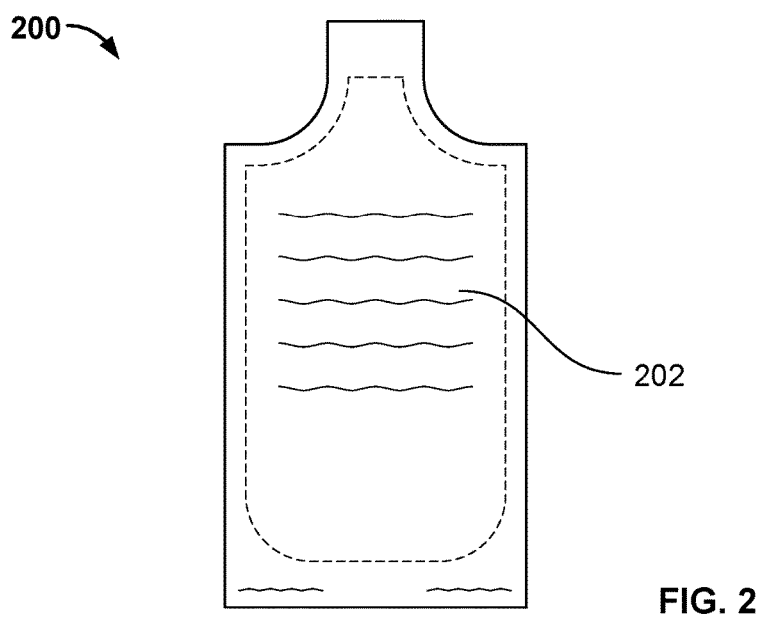
FIG. 2 depicts a packet including a single dose of a neuromuscular aid.

FIG. 2 depicts packet 200 including a neuromuscular aid. As used herein, "packet" generally refers to packaging of any sort designed to contain a quantity of a gas, liquid, solid, gum, candy, thin film, gel, suspension, colloid, aerosol, or the like. Packet 200 may be made of materials including foil, polymer, and paper. Packet 200 may be in the form of a wrapper or sealed packaging. Packet 200 may contain a single dose or multiple doses of a neuromuscular aid. Packet 200 may be opened manually by a user. Packet 200 may be resealable, reusable, disposable, or recyclable.

The neuromuscular aid in packet 200 may be in the form of an oral rinse or a gel. A single dose may include 1 to 50 mL, 3 to 30 mL, or 5 to 10 mL of the neuromuscular aid. Packet 200 includes instructions for use 202. Instructions for use 202 are printed on an exterior of packet 200. When packet 200 includes a neuromuscular aid in the form of an oral rinse, the instructions for use may include instructions to retain the oral rinse in the oral cavity of a subject for a length of time for alleviation or prevention of muscle cramps. In some cases, instructions for use 202 include instructions to expel the oral rinse from the oral cavity after retaining the oral rinse in the oral cavity for a length of time. In other cases, instructions for use 202 include instructions to swallow or ingest the oral rinse after retaining the oral rinse in the oral cavity for a length of time. In certain cases, instructions for use 202 include instructions to gargle with the oral rinse or swish the oral rinse in the oral cavity. In one example, instructions for use 202 include instructions to rinse the oral cavity with the oral rinse for 5 seconds to 120 seconds or up to 60 seconds. In another example, instructions for use 202 include instructions to retain the oral rinse in the oral cavity for a length of time sufficient to alleviate muscle cramps.

An oral rinse provided as a single dose, such as that provided in packet 200, is an aqueous solution including 1 wt % to 15 wt % food grade acid (e.g., 1 wt % to 10 wt %, 2 wt % to 8 wt %, 3 wt % to 6 wt %, or 4 wt % to 5 wt %). The food grade acid includes at least one of acetic acid, citric acid, sulfuric acid, and lactic acid. The oral rinse may include one or more of electrolytes (e.g., potassium, calcium, or sodium), flavorings (e.g., lemon, orange, cinnamon, ginger, berry, or mint), and thickening agents. The oral rinse may be free of sodium (e.g., free of added sodium).

A neuromuscular aid may be used as an oral treatment to treat neuromuscular conditions, such as cramps. An oral treatment method includes administering a composition including 1 wt % to 15 wt % food grade acid to the oral cavity of a subject suffering from muscle cramps, and retaining the oral rinse in the oral cavity for a length of time (e.g., 5 seconds to 120 seconds, 10 seconds to 60 seconds, or until symptoms are alleviated). The method may include expelling the composition from the oral cavity after retaining the composition in the oral cavity for a length of time, or ingesting or swallowing the composition after retaining the composition in the oral cavity for a length of time. The composition may be in the form of a solid, a gum, a powder, a thin film, a gel, or an oral rinse. The composition may include 1 wt % to 10 wt %, 2 wt % to 8 wt %, 3 wt % to 6 wt %, or 4 wt % to 5 wt % of a food grade acid (e.g., at least one of acetic acid, sulfuric acid, citric acid, and lactic acid) and one or more additives (e.g., vitamins, electrolytes, flavorings, and thickening agents).

Although the above description and the attached claims disclose a number of embodiments of the present invention, other alternative aspects of the invention are disclosed in the following further embodiments.

Embodiment 1

A solution of water and food grade acid, such as acetic acid, citric acid, sulfuric acid, lactic acid or other food grade acid, in a concentration between 0.1 and 14.9%.

Embodiment 2

A solution according to Embodiment 1 wherein water soluble vitamins, minerals, viscosity modulator and/or flavoring are included.

Embodiment 3 solid, gum, powder, candy, thin film strip, gel or other object or material that when mixed with the saliva of a subject creates a solution according to Embodiment 1 or 2 either immediately or over a period of time. Its delivery form may also allow it to release a concentration of the solution in Embodiment 1 for an extended period of time, as in time release.

Embodiment 4

A gaseous mixture that delivers acetic acid, citric acid, sulfuric acid, lactic acid or other food grade acid in a concentration between 0.1% and 14% to the mouth of a subject.

Embodiment 5

An aerosol solution that delivers acetic acid, citric acid, sulfuric acid, lactic acid or other food grade acid in a concentration between 0.1% and 14% to the mouth of a subject.

Embodiment 6

A method of applying to the inside of the subject's mouth, and without ingestion, a solution, formula or other product for a particularized period of time in order to deliver its ingredients to receptors located in the mouth or throat of a subject.

Embodiment 7

A method according to Embodiment 6 wherein the subject holds the formula, solution or other product in the mouth without swishing.

Embodiment 8

A method according to Embodiment 6 wherein the subject gargles the formula, solution or other product in the mouth without swallowing.

Embodiment 9

A method according to Embodiment 6 wherein the subject swishes, holds or gargles products identified in Embodiments 1 through 4 in the mouth for a pre-defined period of time.

Embodiment 10

A method according to Embodiment 6 wherein a drug is an ingredient in the formula and is delivered to the receptors in the subject's mouth to treat a disease or condition.

Embodiment 11

A method according to Embodiment 6 wherein a dietary supplement is an ingredient in the formula and is delivered to the receptors in the subject's mouth to treat a disease or condition.

Embodiment 12

A method according to Embodiment 6 wherein a food is an ingredient in the formula and is delivered to the receptors in the subject's mouth to treat a disease or condition. "Food" is defined according to 21 U.S.C. 321(f) as "(1) articles used for food or drink for man or other animals, (2) chewing gum, and (3) articles used for components of any such article."

Embodiment 13

A method according to Embodiment 6 wherein a food additive is an ingredient in the formula and is delivered to the receptors in the subject's mouth to treat a disease or condition.

Embodiment 14

A method according to Embodiment 6 wherein a secondary direct food additive is an ingredient in the formula and is delivered to the receptors in the subject's mouth to treat a disease or condition.

Embodiment 15

A method according to Embodiment 6 wherein a food contact substance is an ingredient in the formula and is delivered to the receptors in the subject's mouth to treat a disease or condition.

Embodiment 16

A method according to Embodiment 6 wherein a colorant and/or color additive is an ingredient in the formula and is delivered to the receptors in the subject's mouth to treat a disease or condition.

Embodiment 17

A method according to Embodiment 6 wherein a medical food is an ingredient in the formula and is delivered to the receptors in the subject's mouth to treat a disease or condition.

Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims.

What is claimed is:

1. A method of treating muscle cramps or pain in a subject, the method comprising:
   administering an oral rinse to the oral cavity of a subject suffering from muscle cramps or pain;
   retaining the oral rinse in the oral cavity for 5 seconds to 120 seconds until the muscle cramps or pain subsides, wherein retaining the oral rinse in the oral cavity comprises holding the oral rinse in the oral cavity, swishing the oral rinse in the oral cavity, or gargling with the oral rinse; and
   after the muscle cramps or pain subsides, swallowing the oral rinse,
   wherein the oral rinse is free of added sodium and is formulated with 3 wt % to 6 wt % acetic acid and at least one ingredient selected from the group consisting of a water-soluble vitamin, a sweetener, a flavoring, and an electrolyte.

2. The method of claim 1, wherein the oral rinse comprises a water-soluble vitamin.

3. The method of claim 2, wherein the water-soluble vitamin is selected from the group consisting of vitamin $B_1$, vitamin $B_2$, vitamin $B_6$, vitamin $B_{12}$, folic acid, pantothenic acid, biotin, and vitamin C.

4. The method of claim 1, comprising retaining the oral rinse in the oral cavity for 10 seconds to 60 seconds.

5. The method of claim 1, wherein the oral rinse comprises a sweetener.

6. The method of claim 1, wherein the oral rinse comprises 0.01 wt % to 0.05 wt % of electrolytes selected from the group consisting of potassium and calcium.

7. The method of claim 1, wherein the muscle cramps or pain is associated muscle spasms, muscle fatigue, headaches associated with muscle tension, premenstrual syndrome, fibromyalgia, or treatments or systemic diseases that cause muscular aches or pains.

8. The method of claim 1, wherein the muscle cramps or pain occurs during sleep.

9. The method of claim 1, wherein the muscle cramps or pain is associated with lower motor neuron disease, upper motor neuron disease, post-poliomyelitis, uremia, cirrhosis, hypothyroidism, pregnancy, diarrhea, or hemodialysis.

10. A method of treating muscle cramps or pain in a subject, the method comprising:
   administering a composition comprising 1 wt % to 15 wt % acetic acid to the oral cavity of a subject suffering from muscle cramps or pain, wherein the composition is formulated as a solid, a gum, a powder, a candy, a spray, an aerosol, or a thin film strip;
   combining the composition with saliva in the oral cavity of the subject to yield a solution; retaining the solution in the oral cavity for 5 seconds to 120 seconds until the muscle cramps or pain subsides, wherein retaining the solution in the oral cavity comprises holding the solution in the oral cavity, swishing the solution in the oral cavity, or gargling with the solution; and
   after the muscle cramps or pain subsides, swallowing the solution;
   and the composition when formulated as a solid other than a gum, a powder, a candy or a thin film strip comprises 4 wt % to 15 wt % of acetic acid.

11. The method of claim 10, wherein the oral rinse further comprises a water-soluble vitamin.

12. The method of claim 11, wherein the composition is a time-release formulation.

13. The method of claim 10, comprising retaining the oral rinse in the oral cavity for 10 seconds to 60 seconds.

14. The method of claim 10, wherein the solution further comprises 0.01 wt % to 0.05 wt % of electrolytes selected from the group consisting of potassium, calcium, and sodium.

15. The method of claim 10, wherein the solution is free of added sodium.

16. The method of claim 10, wherein administering the composition to the oral cavity comprises spraying the spray or aerosol into the oral cavity.

17. A method of treating muscle cramps or pain in a subject, the method comprising:
   administering an oral rinse comprising 3 wt % to 6 wt % acetic acid to the oral cavity of a subject suffering from muscle cramps or pain, wherein the oral rinse is in the form of a suspension, colloid, gel, or carbonated liquid;
   retaining the oral rinse in the oral cavity for 5 seconds to 120 seconds until the muscle cramps or pain subsides, wherein retaining the oral rinse in the oral cavity comprises holding the oral rinse in the oral cavity, swishing the oral rinse in the oral cavity, or gargling with the oral rinse; and
   after the muscle cramps or pain subsides, swallowing the oral rinse.

18. The method of claim 17, wherein the oral rinse further comprises a water-soluble vitamin.

19. The method of claim 18, wherein the water-soluble vitamin is selected from the group consisting of vitamin $B_1$, vitamin $B_2$, vitamin $B_6$, vitamin $B_{12}$, folic acid, pantothenic acid, biotin, and vitamin C.

20. The method of claim 17, comprising retaining the oral rinse in the oral cavity for 10 seconds to 60 seconds.

21. The method of claim 17, wherein the oral rinse further comprises a sweetener.

22. The method of claim 17, wherein the oral rinse further comprises 0.01 wt % to 0.05 wt % of electrolytes selected from the group consisting of potassium, calcium, and sodium.

23. The method of claim 17, wherein the oral rinse is free of added sodium.

24. A method of treating muscle cramps or pain in a subject, the method comprising:
   administering an oral rinse to the oral cavity of a subject suffering from muscle cramps or pain;
   retaining the oral rinse in the oral cavity for 5 seconds to 120 seconds until the muscle cramps or pain subsides, wherein retaining the oral rinse in the oral cavity comprises holding the oral rinse in the oral cavity, swishing the oral rinse in the oral cavity, or gargling with the oral rinse; and
   after the muscle cramps or pain subsides, swallowing the oral rinse, wherein the oral rinse is formulated with 3 wt % to 6 wt % acetic acid, an artificial flavoring, and at least one ingredient selected from the group consisting of a water-soluble vitamin, a sweetener, and an electrolyte.

25. The method of claim 24, comprising retaining the oral rinse in the oral cavity for 10 seconds to 60 seconds.

\* \* \* \* \*